United States Patent
Papas et al.

(10) Patent No.: US 7,236,817 B2
(45) Date of Patent: Jun. 26, 2007

(54) ANIMATION TECHNOLOGY

(75) Inventors: Sam Papas, Adelaide (AU); Michael John Sandow, Adelaide (AU)

(73) Assignees: True Life Creations (SA) Pty Ltd., Adelaide, South Australia (AU); Macropace Products Pty Ltd., Adelaide, South Australia (AU)

( * ) Notice: Subject to any disclaimer, the term of this patent is extended or adjusted under 35 U.S.C. 154(b) by 627 days.

(21) Appl. No.: 10/220,866

(22) PCT Filed: Mar. 5, 2001

(86) PCT No.: PCT/AU01/00229

§ 371 (c)(1),
(2), (4) Date: Sep. 3, 2002

(87) PCT Pub. No.: WO01/64106

PCT Pub. Date: Sep. 7, 2001

(65) Prior Publication Data
US 2003/0023156 A1     Jan. 30, 2003

(30) Foreign Application Priority Data
Mar. 3, 2000    (AU)  ................................... PQ6001

(51) Int. Cl.
*A61B 5/05*     (2006.01)
(52) U.S. Cl. ...................... 600/427; 600/407; 600/410; 600/425; 703/2; 382/131
(58) Field of Classification Search ...................... None
See application file for complete search history.

(56) References Cited
U.S. PATENT DOCUMENTS
5,154,178 A * 10/1992 Shah .......................... 600/415
5,825,908 A * 10/1998 Pieper et al. ................ 382/131
6,161,080 A * 12/2000 Aouni-Ateshian et al. .... 703/11
6,450,978 B1 * 9/2002 Brosseau et al. ............ 600/595

OTHER PUBLICATIONS

Thybout M. Moojen, MD et al, In Vivo Analysis of Carpal Kinematics and Comparative Review of the Literature, The Journal of Hand Surgery, Jan. 1, 2003, pp. 81-87.

* cited by examiner

*Primary Examiner*—Eleni Mantis Mercader
*Assistant Examiner*—James Kish
(74) *Attorney, Agent, or Firm*—Klauber & Jackson

(57) ABSTRACT

A method for creating an animated image of the bones of a body part is described. The steps include converting Computed Axial Tomography (CAT or CT) scan and Magnetic Resonance Imaging (MRI) 2-dimensional cross-sectional images (slices) into 3-dimensional images of individual bones (FIG. 1). A first ordered series of slices of a body part in a first position is converted into a 3-dimensional representation of the skeleton of the body part and then a second ordered series of slices of the same body part in a different position is converted. The converted images are then used to create a step frame animation of the movement of the skeleton of the body part. Additional ordered series of slices of the body part in other intermediate positions could be used in the step frame animation. The steps of the method may also include the process of separating the bones if they are depicted as co-joined in a slice (FIGS. 6 and 7). The method can also include the identification of isometric points (FIGS. 8 to 11) on the separated bones to aid a clinician in the diagnosis of a problem or abnormality as well as assist in the application of "what if" surgical procedures on the digital representation of the skeleton of the scanned body part. The method can also include steps that create movement of the bones of the body part by applying rules of motion for one or more points on the separated bones of the scanned body part.

12 Claims, 6 Drawing Sheets

ANIMATION TECHNOLOGY

ANIMATION TECHNOLOGY

This invention relates to 3-dimensional analysis of the human skeleton and in particular provides a method for improved clinical diagnosis and repair of associated soft tissue injuries and abnormalities using existing imaging equipment.

BACKGROUND

Computed Axial Tomography (CAT or CT) scan and Magnetic Resonance Imaging (MRI) technologies provide detailed 2-dimensional cross-sectional images or "slices" of the human body. The 2-dimensional slices are viewable by clinicians and a diagnosis can be made.

Of more usefulness to clinicians is the provision of computed 3-dimensional images of the human body.

CAT/CT and MRI equipment is highly specialised and the digital output of each "slice" is typically provided in proprietary digital image format for use by the manufacturers image manipulation software and hardware to produce 2-dimensional and computed 3-dimensional representations for display on a screen constructed "slices" produced by the CAT/CT and MRI equipment. These images are referred to as solid-form images and can be made to depict bones, ligaments, blood vessels, muscles and tendons according to various settings available on the imaging equipment.

Each set of images typically only depicts the stationary condition of the part of the patient being examined.

Thus, analysis of the information provided by such images can only provide a limited part of the clinical basis for a diagnosis as to the problem or abnormality associated with the scanned body part.

The discussion herein providing some background to the invention is intended to facilitate a better understanding of the invention. However, it should be appreciated that the discussion is not an acknowledgment or admission that any of the material referred to was published, known or part of the common general knowledge as of the priority date of the application.

The invention described in this specification provides a means and method for the visualisation of information generated by current CAT/CT and MRI equipment. This will enable more accurate and "what if" manipulation of the digital image of a 3-dimensional representation of the scanned body part so as to improve the accuracy of diagnosis by the clinician. It will also improve the probability of the success of planned corrective surgery via manipulation of the three-dimensional representation and analysis of the resultant movement.

BRIEF DESCRIPTION OF THE INVENTION

In a broad aspect of the invention, a method of producing 3-dimensional visualisations of digital representations of cross-sectional slices of a vertebrate animal or human body part includes the steps of:
a) obtaining a first ordered series of slices of a portion of said body part in a first position;
b) applying one or more filters to each of said digital representations of said first ordered series of slices to identify the skeletal portions of said body part;
c) converting said first filtered series into a 3-dimensional representation of the skeleton of said body part in said first position;
d) obtaining a second ordered series of slices of said portion of said body part in a second position different to said first position wherein said first and said second position of said portion of said body part is representative of extremes of the achievable movement of said portion of said body part;
e) applying one or more filters to each of said digital representations of said second ordered series of slices to identify the skeletal portions of said body part;
f) converting said second filtered series into a 3-dimensional representation of the skeleton of said body part in said second position;
g) combining said 3-dimensional representations to form a step frame animation having as many steps as there are ordered series of slices.

A yet further aspect of the method includes the further step of:
h) obtaining a one or more further ordered series of slices of said portion of said body part in a one or more further positions;
i) converting said further filtered series into a 3-dimensional representation of the skeleton of said body part in said further positions;
j) combining said 3-dimensional representations to form a step frame animation having as many steps as there are ordered series of slices.

In a yet further aspect of the invention the method includes the further step of:
k) selecting a plurality of points on two or more skeletal object s in each said 3-dimensional representation; and
l) analysing whether the distance between pairs of said points on different skeletal objects are isometric, if the distance between pairs of points remain the same or within a predetermined variance of distance during said step frame animation.

In a further aspect of the invention comparing the changes, if any, of the distances between predetermined pairs of points with expected changes, wherein the result of said comparison provides assistance to a clinician to form a diagnosis regarding the body part.

In a further aspect of the invention wherein the isometric points determined equate substantially to the fixation location of the ends of ligaments associated with said portion of said body part and the further step of:
m) comparing the isometric points determined to predetermined isometric points of a typical or contra-lateral body part and if said isometric points vary, a clinician may infer a problem or abnormality and a degree of problem or abnormality associated with one or more ligaments associated with said portion of said body part.

In a further aspect of the invention step b and/or e includes a filter that allows an anatomically knowledgable medical professional to adjust the bone selection criteria of said filter until a representation of adjacent bones shows that said adjacent bones are separate from one another.

In a further aspect of the invention wherein the digital representation of slices of a vertebrate animal or human body part is provided by CAT/CT or MRI apparatus.

In another broad aspect of the invention a method of producing 3-dimensional visualisations of digital representations of cross-sectional slices of a vertebrate animal or human body part includes the steps of:
a) obtaining a first ordered series of slices of a portion of said body part in a first position;

b) applying one or more filters to each of said digital representations of said first ordered series of slices to identify the skeletal portions of said body part;

c) converting said first filtered series into a 3-dimensional representation of the skeleton of said body part in said first position;

d) obtaining a second ordered series of slices of said portion of said body part in a second position wherein said first and said second position of said portion of said body part is representative of extremes of the achievable movement of said portion of said body part;

e) applying one or more filters to each of said digital representations of said second ordered series of slices to identify the skeletal portions of said body part;

f) converting said second filtered series into a 3-dimensional representation of the skeleton of said body part in said second position;

g) applying to one or more points on the skeleton of said body part of each said 3-dimensional representation, one or more rules based animation constraints;

h) creating a 3-dimensional animation of the movement of said body part according to said constraints.

Specific embodiments of the invention will now be described in some further detail with reference to and as illustrated in the accompanying figures. These embodiments are illustrative, and are not meant to be restrictive of the scope of the invention. Suggestions and descriptions of other embodiments may be included but they may not be illustrated in the accompanying figures or alternatively features of the invention may be shown in the figures but not described in the specification.

DETAILED DESCRIPTION OF EMBODIMENTS OF THE INVENTION

By way of example only an embodiment of the invention will be described herein using the bones of the hand as the scanned portion of the human body. However, this should in no way limit the application of a suitable scanning apparatus and the methodology of the invention to just that part of the body. Indeed it is possible that the method can be used on any portion of any vertebrate animal or human.

By way of assistance various bones of the hand and in particular, the wrist are referred to throughout this description, so a brief explanation of the various bones of the wrist is provided herewith.

Figure 1:
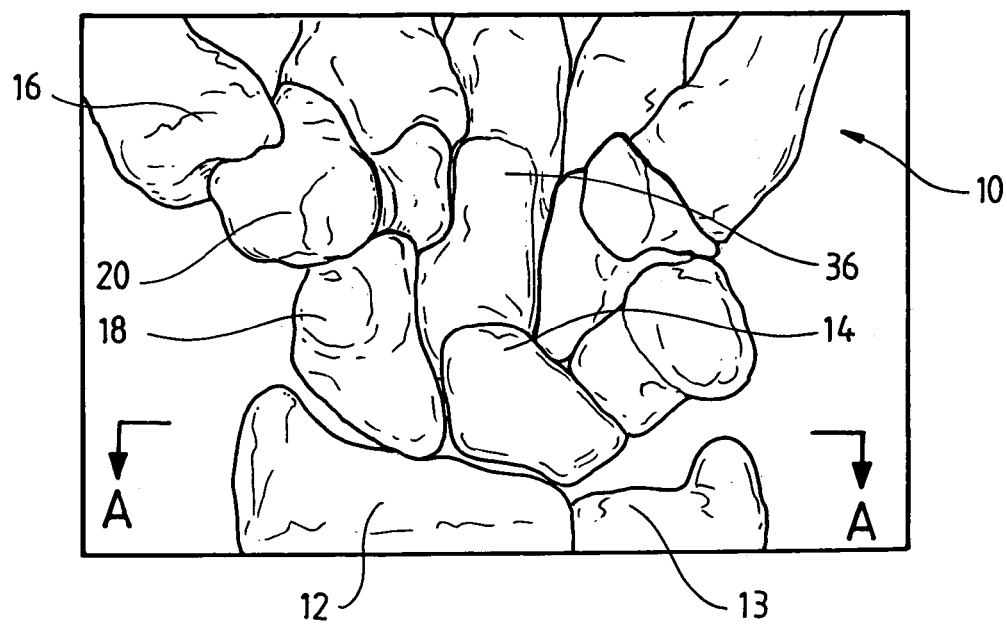
FIG. 1 is a front view of the radius and carpal bone.

FIG. 1 depicts an image obtained from a CT scan workstation of the wrist also referred to as the carpus. This image is merely a computer generated 2-dimensional representation of the 3-dimensional information collected by the scanning apparatus. The bones depicted are as they are seen from one point of view and it is not possible to observe their individual or interrelated movement.

This view shows the palm facing orientation of the wrist. The distal end of the radius 12 is shown at the lower left-hand side of the image. The distal end of the ulnar 13 is shown at the lower right-hand side of the image.

Central within the carpus lies the lunate 14 (a crescent shaped bone) which appears, from motion studies possible with the method of the invention, to be extremely mobile in flexion, extension and translation, even though it is clearly a load bearing bone and remains well aligned under such load.

Adjacent to the lunate 14 towards the metacarpal 16 of the thumb (pollex) lies the scaphoid 18 (a boat-shaped bone) which is the most lateral bone in the proximal row of the carpal bones. The scaphoid not only translates but also rotates during lateral motion of the wrist.

Above the scaphoid 18 and below the metacarpal 16 of the thumb lies the trapezium 20 (an irregular four sided bone).

Various features of the invention will be described by closely examining images of the carpus and in particular the lunate 14, scaphoid 18 and the trapezium 20 bones of the carpal column. However, it should be understood that this body part and these particular bones are used by way of example only. Only by exercising the invention can the complex interrelationship between various bones and their surrounding body parts become more apparent.

The 2-dimensional image provided by FIG. 1 can be generated in a conventional manner using any one of the medical imaging apparatus currently available. Amongst them, the most commonly used are Computed Axial Tomography (CAT) and Magnetic Resonance Imaging (MRI).

CAT scanning involves the creation of cross-sectional images of a portion of the human body made by accurately rotating an X-ray source and recording the image captured with a radially opposite detector. The cross-sectional image is referred to as a "slice" and although of some use to the clinician, a single slice image may be more useful if arranged as a series of adjacent slices, which are simultaneously made available for viewing by the clinician. Computers are used to create a 3-dimensional representation and an example is displayed in FIG. 2.

Figure 2:
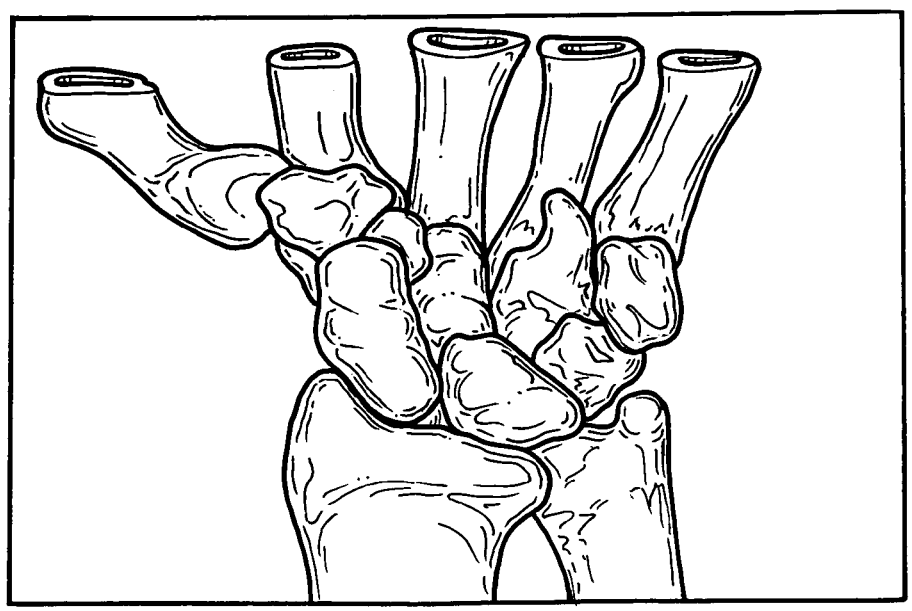
FIG. 2 depicts a front view of a 3-dimensional representation of the radius and carpal bone.

The 3-dimensional representation of the scanned portion of the human body is provided in a 2-dimensional form as a result of a digital transformation of an ordered series of all of the available slices recorded by the CAT equipment. Such images are generated by transforming the different densities of materials recorded in the slice into representations of the various bodily elements bone, tendons, veins etc. FIG. 2 is an example of this but the body part represented is unitary, that is none of the identifiable bones can be separated from the representation for analytical or other purposes.

Similar visual representations are available from MRI equipment where selectively detectable nuclear magnetic resonance of protons produces proton density maps of selected portions of the human body.

The radiant flux densities emitted by these types of equipment are sufficient to provide adequate quality slices for clinical use. For both the abovementioned equipment, flux densities are ever decreasing such, that it has only been recently possible for multiple images to be taken at the same time while maintaining the radiation dosage into the person below safe levels. Such a development thus makes it possible to capture the scanned body portion in multiple positions.

The equipment that provides 3-dimensional representations of the slices is proprietary and inextricably linked to the slice generating equipment. Therefore it tends to be expensive and lacks the ability to provide clinically useful options.

The point of view provided in the 3-dimensional representation can be changed about a reference point chosen within the 3-dimensional space occupied by the representation. The point of view can be any point on a sphere of any diameter about the chosen reference point and by appropriate manipulation the clinician can observe the static relationship of each bone with another. The bones as displayed, are in the position they had during the capture of the CT slices used to create the image.

Clearly, such a view can be very useful for a clinician as an abnormality can be more readily identified as it may be observed from many perspectives unlike the 2-dimensional view of FIG. 1.

However, the image is static, it does not indicate in any way how the bones move in their damaged state nor does the image allow comparison with the movement of a contra healthy limb.

These limitations are part of the problem addressed by the invention. A patient presenting with a problem is physically assessed by a medical professional and if warranted a particular body part is scanned using CAT/CT or MRI equipment. If should be noted however, that the invention is not limited to only these types of scanning equipment.

Figure 3:
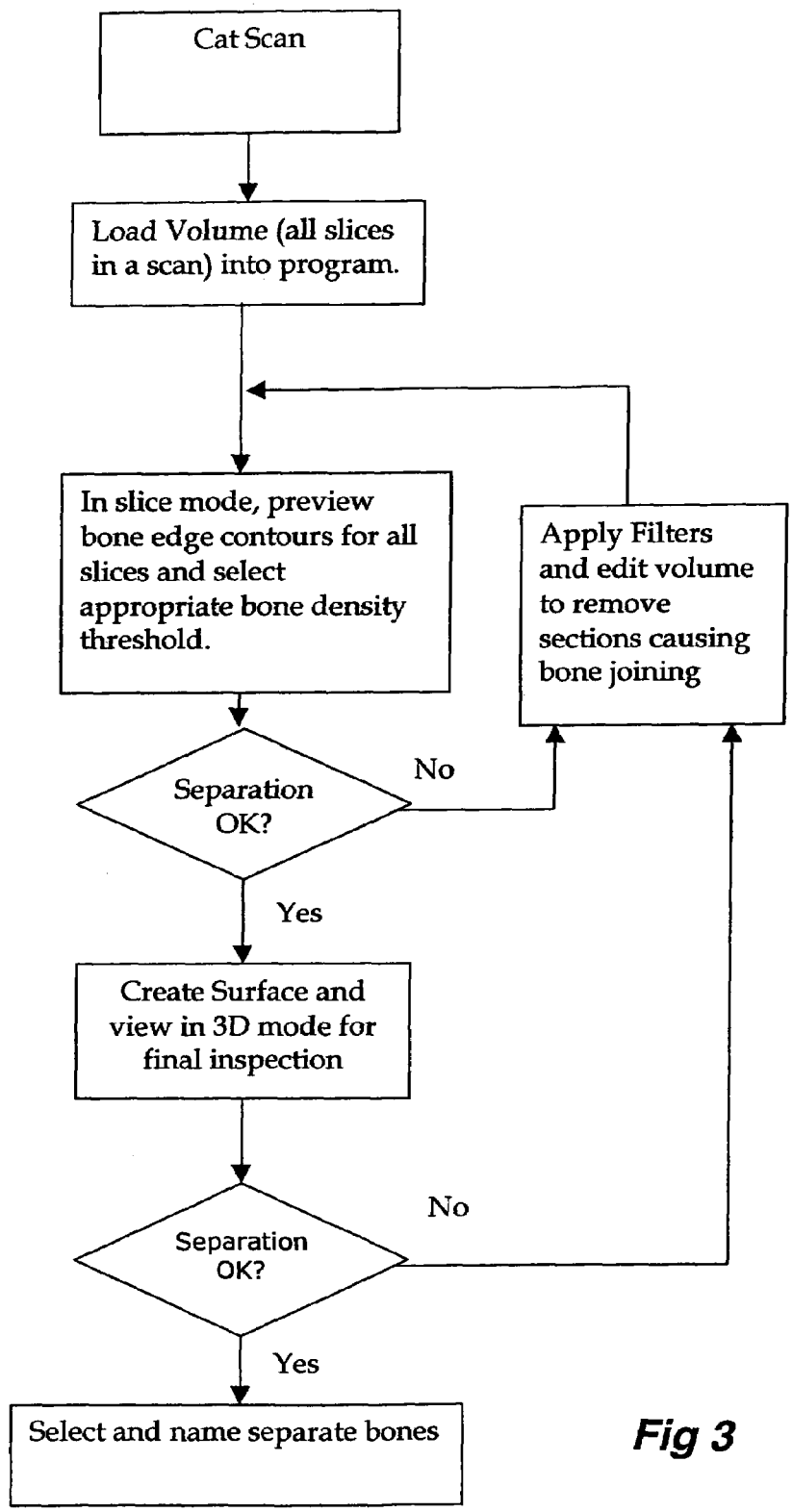
FIG. 3 depicts a flow diagram of an embodiment of the steps performed to create a visual representation of separate bones of a scanned body part.

Referring to FIG. 3, which depicts a preferred embodiment of the steps performed to create a visual representation of separated bones of a scanned body part.

Scanned information is collected and made available as a series of DICOM (Digital Imaging and Communications in Medicine) formatted image slices of the limb or body part requiring investigation by the medical professional.

DICOM formatted output is available from most CAT/CT and MRI equipment. The DICOM format has become popular with medical users as a result of the pressure placed on medical equipment manufacturers to provide a vendor independent digital imaging format. Version 3.0 is currently in place.

The DICOM image slices provided are representative of the body part while in a predetermined position.

Figure 4:
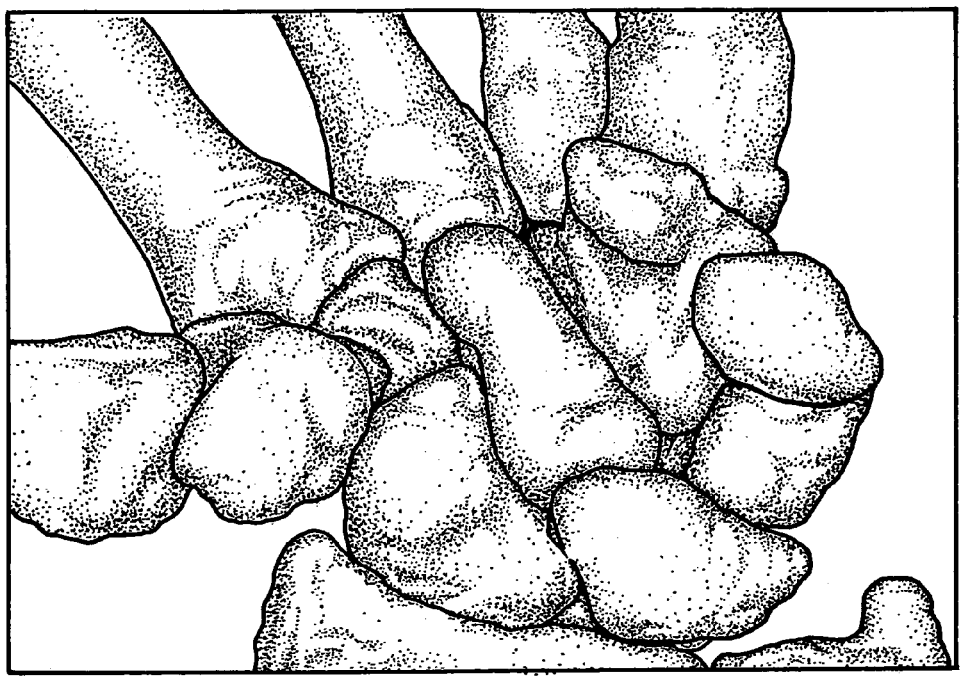
FIG. 4 depicts the wrist in extreme radial deviation.

In this embodiment, the example provided and illustrated in FIG. 4 is of the extreme radial deviation of the wrist. This position of the wrist is achieved by placing the wrist and palm onto a flat surface and moving the hand in the direction of the thumb to its fullest extent. This brings the thumb 16 radially about the wrist and laterally of the radius 12. The series of slices, which are taken at about 1 mm distances apart, can total about 50-60 in the example given, ie. 5-6 cm's of the wrist is scanned for investigation.

Figure 5:
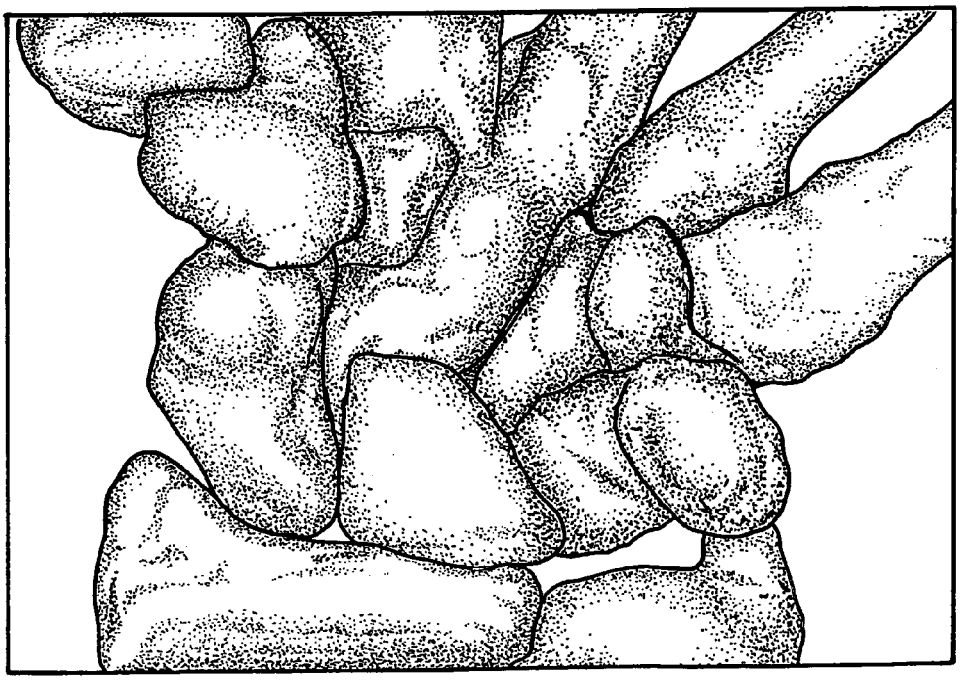
FIG. 5 depicts the wrist in extreme ulnar deviation.

A further step is to record a second series of DICOM formatted image slice data for the same limb or body part in a second position. In this embodiment the second position is the extreme ulnar deviation as depicted in FIG. 5. This position is achieved by moving the palm and wrist in the direction of the little finger to its fullest extent. This brings the little finger in an arc towards the ulnar 13.

It is also possible for a plurality of intermediate positions to be recorded. Five intermediate positions have been found adequate for advanced aspects of the invention to be described later in the specification.

Alternatively, and in accord with the usefulness of extending and flexing the wrist for movement and other analysis, the first and second positions could be full extension and flexion of the wrist.

Extension and flexion of the wrist is achieved for the purposes of scanning, by placing the little finger or the thumb (but preferably the little finger) onto a flat surface with the palm of the hand vertical with respect to the flat surface from which the scanned image is detected. The fingers and thumb are kept in constant spatial relationship with each another while the hand is flexed (turned inwards) to its extreme and then moved to an extension position (bent backwards).

Again, it is possible for a plurality of intermediate positions to be recorded.

In this embodiment, DICOM formatted slices of the various positions are preferable, but other formats can be adapted, as required, for the purposes of this invention.

The next step is to convert the raw DICOM formatted slices to a 3-dimensional surface representation, which depending on the application program used could output stereo lithographic formed files (typically having a .stl file type).

Alternatively, the conversion could take the DICOM formatted slices to a .dfx or .igs file format.

Each set of slices for each position recorded by the CAT or MRI apparatus is converted according to the following steps to provide a 3-dimensional surface representation of the body part that comprises individual bones capable of being represented independent of each other and shown moving according to their actual motion.

However, to achieve that goal, it is in this embodiment, required to have each slice previewed by an appropriately skilled medical professional.

Each DICOM image is provided as a rasterized DICOM format data file and each pixel in that file will have a numerical value representative of the density of the tissue. DICOM files are typically viewed as a grey scale representation and use a 16-bit value representative of density. Hence each pixel has a numerical value and by way of its method of is representative of a grey scale value of tissue density. In the inventor's experience, a numerical scale of 0 to about 1400 is representative of the number if grey scale values evident in the DICOM files but this may be different to the experience of others.

The inventors have also noticed from examination of numerous DICOM slices that bone density appears to fall mostly within the range 1100 to 1300 and recognition of this factor is useful when bone-rendering calculations are preformed as part of the invention to be described later in this specification.

In this embodiment software may be used to initially analyse the series of DICOM formatted slices to determine which pixel's are representative of the different densities of material in the slice and in particular to automatically identify those pixel's which are bone.

For example, if the shape of a cross-section of bone/s is to be automatically determined in each slice, it will be necessary of the program to identify a pixel value or preferably a range of pixel values that represent the bone in the image.

Typically, lighter pixels are likely to be representative of the bone whereas darker pixels are likely to be representative of the lower density of the surrounding tissue but a range of pixel values will most likely be bone of slightly different density.

In the step of identifying pixels likely to be bone, it is preferable to select a range of pixel values say, between 1100 and 1200 that the computer program can use in an initial identification step. When those pixels are identified, as is done in FIG. 6 it will be noted that the bone boundary is clearly identifiable from its surrounding.

However, apart from any characteristics of the CAT or MRI scanning process for example lack of resolution, bones in the patient being scanned may have various densities so the DICOM format data will disclose this variation. There can also be calcification of non-bone tissue that may have similar densities to surrounding bone and other variations of bone densities caused by osteoporosis typically the result of the age of the patient. Such variants of bone and other tissue density can result in some mis-identification by the program of what is and is not bone.

Figure 6:
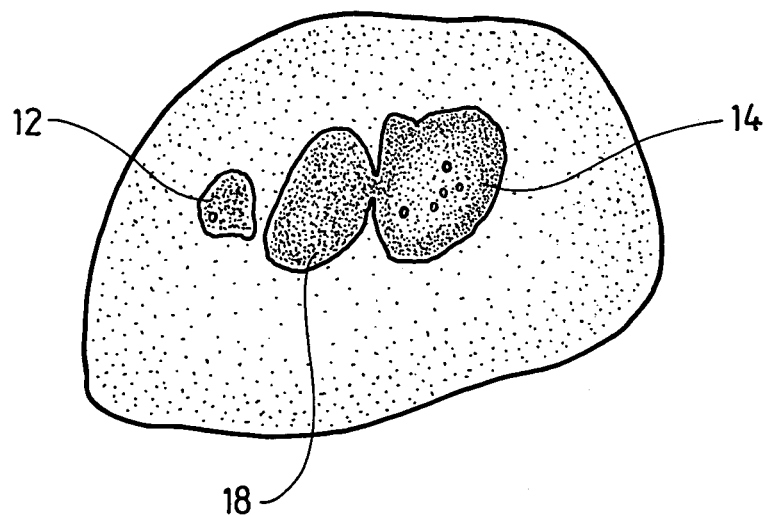
FIG. 6 depicts cross-section A-A of FIG. 1 showing a portion of a poly frame representation of co-joined bones overlayed on the cross-section.

FIG. 6 is a pictorial representation of a section A-A of FIG. 1. FIG. 6 depicts a 2-dimensional top view of a slice through a wrist and a cross-section of the various bones of the carpus can be seen. In particular the distal end of the radius 12, the scaphoid 18 and the lunate 14.

The human eye is an excellent tool for performing an analysis of what particular grey scale value is representative of the bony portions of the slice and those of the surrounding tissue but more particularly for identifying what is likely to be bone and what is not. A computer however, deals with the values of every pixel and discrimination is a purely mathematical process. Thus, even though the speed and accuracy of the computer is of assistance in making an initial determination, the logical rules followed by the computer are not always useful in terms of their results.

It is therefore necessary to combine the effort of a computer with that of a skilled human in identifying in each slice the difference between bone and surrounding tissue. This is especially so when the computer generated representation of adjacent bones sometimes looks as if the bones are fused when indeed they should be separate from each other as is illustrated in FIG. 6 where the scaphoid 18 appears to be fused to the lunate 14. A skilled human can assist the computer to separate bone from bone as well as surrounding tissues from bone, that would otherwise be considered by the computer to be one bone or a bone having an atypical shape.

As indicated previously, FIG. 6 pictorially depicts how a computer analysis indicates adjacent bones, the lunate 14 and the scaphoid 18 are co-joined. This is not the case in a typical patient and it is therefore necessary for this representation to be modified by the clinician to separate the bones.

Once the two bones are completely separated at the slice level it will be possible to depict them independently of each other and independent of other elements by using computer surface rendering tools to create a 3-dimensional representation. In particular the independent movement of each bone will be made possible once they have been separated.

The process of bone to bone separation can be best done with the input of a clinician or medical professional having appropriate anatomical knowledge. It anticipated that if the clinician can become involved at that stage of the process it will be beneficial to the utility of the method and ultimately beneficial to the patient. It is thus of some importance that the useability of the software at this stage of the process is preferably as simple and reliable as it can be.

Figure 7:
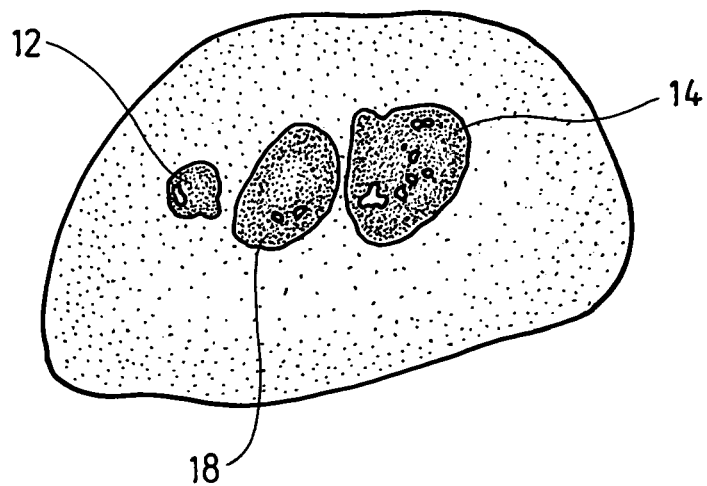
FIG. 7 depicts a portion of a poly frame representation of separated bones overlayed on the cross-section of FIG. 6.

FIGS. 6 and 7 show the same slice and it may be necessary for a person or persons to examine and if necessary modify every one of the tens or hundreds of slices that make up the basis for a 3-dimensional model of the body part being examined.

That is however unlikely as the slices which show co-joined bones are typically a small proportion of the total number created.

FIG. 3 indicates that a further step in this embodiment of the invention is for the clinician to varying the predetermined bone density range or upper or lower setting. The computer program will display the bone shape with greater or lesser degrees of merger with its adjacent bone until the bones appear separated.

The application of various filters to the DICOM data file can improve the computer's attempt to separate bones from one another. However, bones are not the only part of the body that can be identified and separated using such filters. Ligaments and tendons will have a different density to surrounding tissue and bones and thus appropriate choice of density (pixel value or range of values) will allow the computer to discriminate these other types of body parts for construction into specific 3-dimensional images relating to that chosen element.

These filters can be applied to the entire volume (all slices) or to a sub-volume (single slice, part of a slice or a part of more than one slice).

For example, a filter may only need to be applied to three or four slices in a series.

One preferred method of presenting the computer's separation effort for review by an appropriate medical professional is to display the individual slices as raster images. This is shown FIGS. 6 and 7 where a cross-section of the computer generated 2-dimensional surface of the bone is overlayed as a result of the choice by the clinician of the predetermined bone density or density range (ie. grey scale value or range) to be used.

The 2-dimensional cross-section described is a poly line that represents in the worst case, joined areas of two adjacent bones as illustrated in FIG. 6. This representation is created because the source slice as examined by the computer, has areas of the same or similar density that are interpreted by he computer to be bone.

The user in this embodiment, and of course there are alternative methods, is able to vary the pixel value range that represents bone in the raster image. Areas between the two bones are likely to have values that will fall outside the predetermined range, such that when the computer reviews that slice again it will use the now adjusted bone density regions to construct its 2-dimensional representation of the now separate bones.

It helps and it is preferable that these modifications by the user are applied immediately to the 2-dimensional representation of the bone shape so that the result of the modification can then be viewed immediately by the medical professional. It is particularly useful for the before and after images such as FIGS. 6 and 7 to be displayed adjacent to each other.

When any filtering or density adjustment is done, it is preferable to continue to use the computer's rules to identify bone so as to maintain the characteristics of the 3-dimensional representation. This rule therefore acts as a check against totally incompatible modifications. Thus it is preferable for the user to vary a range of the pixel vales that represent non-bone rather than simply removing pixels. If pixels were merely removed from the rasterized slice the 2-dimensional representation of the bone wall may well be missing so much information that it may be difficult to generate an acceptable 3-dimensional representation when surface rendering tools are applied.

That is, a surface-rendering tool can be programmed to use the density variation of the outer wall of the bone to better define its outer surface. Say for example, the outer wall of bone has pixel values between 1150 and 1250 and that the density varies linearly with in that range. The surface-rendering tool will use these rules to create a more accurate representation of the surface of the bone because it can be determined with greater surety than otherwise would be the case. When a clinician merely eliminates/erases pixels that lie between bone it is likely that the surface-rendering tool will produce a less representative and likely jagged representation of the bone surface. This occurs because some of the erased pixels are actually bone and others were part of the transition of density values representative of the bone.

One further way of performing the process of separating bone, is to display the result of the computer's analysis in pictorial 3-dimensional form and allow the medical professional to adjust the shape of the displayed parts. This option however may allow the professional to dramatically stray from the information contained within the DICOM slices. Depending on how the software is set up such an approach may be possible within certain limits. Once a co-joined bone region is identified, the medical professional can designate with a pointing device the relevant area that needs to be modified. This process would be performed on the imperfect 3-dimensional surface mesh created by the computer until it was thought to more closely represent the patient's body part, which it would within the limits of the program's ability to take the DICOM data into account.

Once all the bones are isolated with either of the methods described above, it is possible for the program to surface render regions identified as and for the medical professional to select them and name them, refer to FIG. 3.

It is also then possible for the medical professional, particularly clinicians, to manipulate the 3-dimensional image in ways that more readily identify the damage or disease affecting that particular body part. It will also be possible for the clinician or medical professional to remove one or more bones from the 3-dimensional representation, so that the shape of bones beside and behind a removed bone can be more readily observed.

It is also possible to use colour to identify the different bones and more readily examine the motion or immobility as the case may be of the injured or diseased portion of the body.

In this format it is possible to create a spatial reference point relevant to the body part being displayed. For example, in the wrist it could be a well-known point on the distal end of the radius 12.

Once the fixed point is determined each 3-dimensional representation can be linked via that reference point to each other representation. This method of linking the individual representations is but one available to those skilled in the art of digital image display and manipulation, so that relative positions and in an advanced aspect of the invention, motion of bones can be referenced for an observer.

If the steps disclosed in FIG. 3 are repeated for the various CAT/CT and MRI scans of the body part in different positions it will be possible to place each 3-dimensional representation of the body part in a step frame animation sequence and replay the motion of the body part between the various positions recorded.

A total of seven positions should be adequate to provide the viewing clinician a much better understanding of the relevant movement of the bones of the wrist. The clinician will be able to observe the movement of a bone relative to others as they move and if necessary view those same motions from various points of observation.

Furthermore a digitally created image such as a 3-dimensional surface representation of various bones can be manipulated in many ways.

For example, since each bone is displayed as a group of pixels representative of a 3-dimensional surface, the bone represented by that surface may be manipulated as a whole.

In one example, a particular bone can be deleted from view, without interfering or changing the representation of other bones in the display. Thus by removing all the bones except the scaphoid 18, the radius 12 and the ulnar 13 it is possible to view all of the distal and radial surfaces of the scaphoid, as it moves and interacts with adjacent bones including the bone/s deleted from view. Furthermore, once in the digital environment it is possible to remove all the surrounding bones so the clinician can obtain a 360° view of the scaphoid and thus be much better informed when providing a diagnosis of the problem and prognosis for its solution.

Clearly, the ability to manipulate the image in this and related ways can be useful to the clinician, but there are other features of the invention which will further assist clinicians and surgeons.

The inventors have identified that once the 3-dimensional surface representations have been created, it is also possible to accurately analyse the motion of each bone.

It has also been realised, that whereas the bones provide the skeletal anatomy of the human body, the ligaments determine the functional movements of the human body. Extrinsic loads on the bones are created by the action of muscles attached to specific bones wherein the various loads are counter balanced by ligaments in a non-obvious way. Thus to explain the reason certain bones or a collection of bones move in a certain way it is necessary to know how the many associated ligaments interact with those bones.

The location of various ligaments on a bone is known primarily from dissections during surgery and more particularly from studies of cadavers. Cadaver studies have revealed some of the functions of certain ligaments but those studies are not ideal due to an inability to adequately replicate the extrinsic loading of ligaments in the absence of live muscle tissue.

The inventors surmise however that ligaments provide the ability for bones to achieve their complex orientation and movement by tethering to and in most instances checking the motion of various points on the surface of the bone.

Ligaments remain under minimum tension and with oblique complex orientation along with the shape of the bone create a working environment that individualises the anatomy so as to achieve the final motion of the body part of that particular person.

Ligaments also provide positional feedback to allow for the control of the motion of the carpal bones via proprioception. That is, the reception by sensory nerve terminals within the muscles of the arm and the various receptors in the wrist, provide information to the body as to the position and relative motion of the wrist.

Thus the inventors have found that it is possible to infer the function of various ligaments by knowing the position of various isometric points that exist in any set of bones in a particular body part.

Typically ligaments will extend between carpal bones to and from points which remain a fixed distance from each other during motion of the bones of the carpal column. These points are isometric as they exist solely as result of the action of ligaments and bone shape. Thus such points could be considered the basis of isometric constraints on bone movement. In any event the identification of isometric points enables rules of motion for bones and groups of bones to be formulated, more about which will be described later in the specification.

Figure 8:
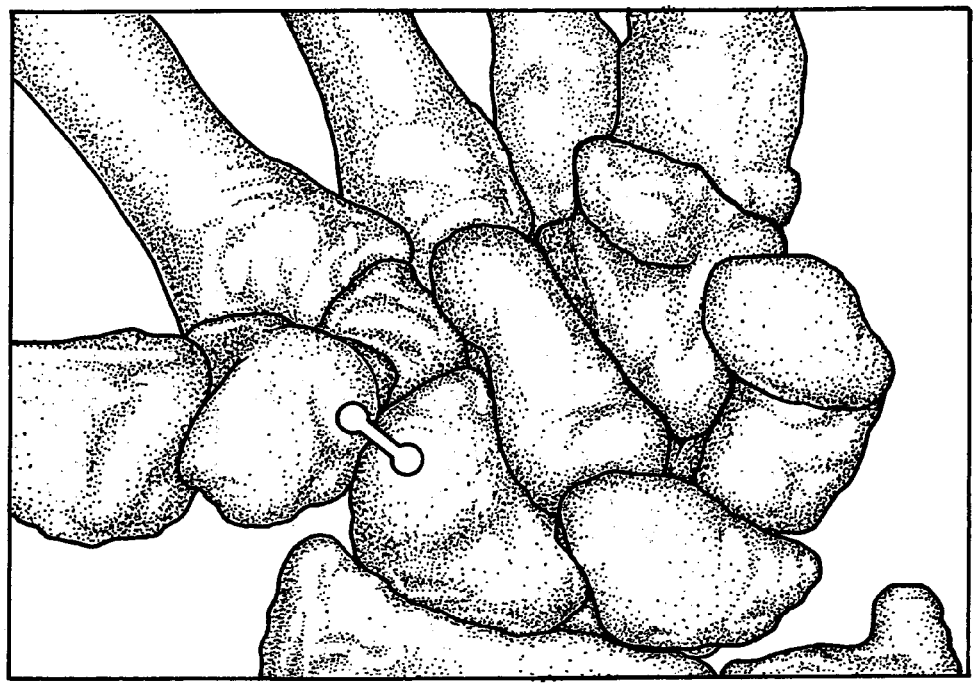
FIG. 8 depicts a front view of a wrist showing isometric points between the scaphoid and the trapezium bones while the wrist is in extreme radial deviation.

Referring to FIG. 8 two points are shown, one on the scaphoid 18 and the other on the trapezium 20 with a line extending between them.

Figure 9:
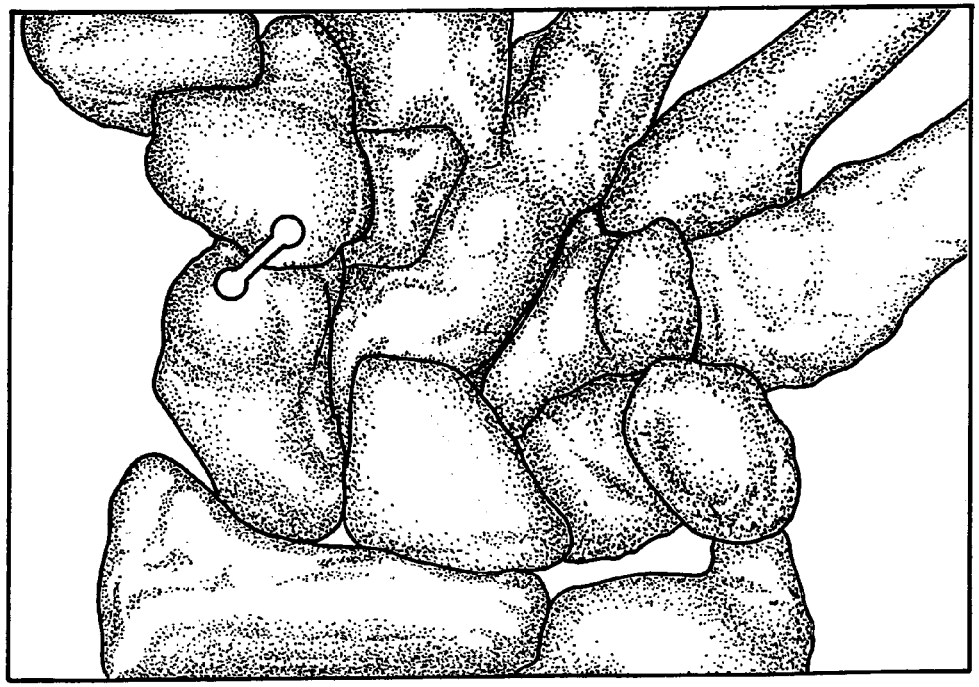
FIG. 9 depicts a front view of a wrist showing isometric points between the scaphoid and the trapezium bones while the wrist is in extreme ulnar deviation.

Referring to FIG. 9 the same two points as shown in FIG. 8 is shown one on the scaphoid 18 and the other on the trapezium 20 with a line extending between them.

A program set up specifically to choose such points identified this pair of points. The program is able to check many pairs of points on the representative surface of the bones and pairs of points that remain a fixed distance from each other during motion are identified. Clearly, there are many ways in which such a programming function could be performed to provide a collection of paired isometric points.

A preferable methodology is to identify a first point in 3-dimensional space that lies on the surface of a bone say the scaphoid 18 and calculate the distance to a plurality of points on the surface of another bone say the trapezium 20 while the bones are in one position, eg while the wrist is in a first position (the extreme radial deviation). It is then possible to recalculate the distances between those points at a second position (the extreme ulnar deviation). The distance between the chosen point on the trapezium and a point on the scaphoid that remains the same distance as the first measurement identifies an isometric pair of points. The distance measurement need not be exact to the mm and a range of variation would be acceptable. Thus isometric points will become isometric regions in one embodiment of the arrangement.

The same analysis can be carried out between a variety of points on different bones of the carpus. Clearly a computer program is best suited to such a task as there are many thousands of such points to be analysed.

Figure 10:
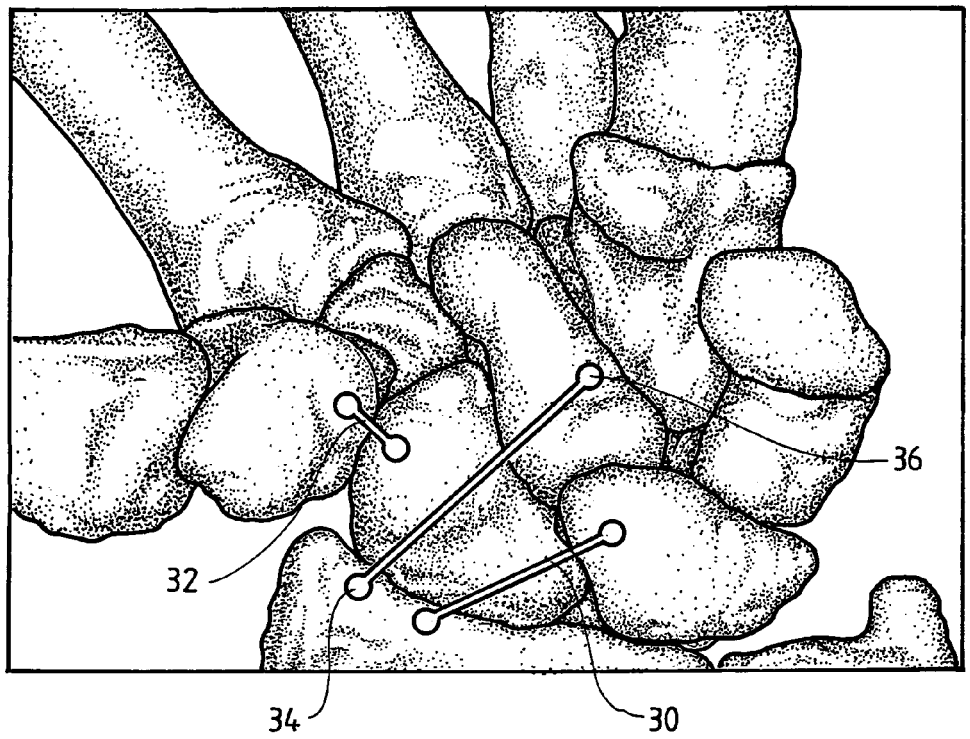
FIG. 10 depicts isometric points of the lateral carpal column of the wrist in extreme radial deviation.
Figure 11:
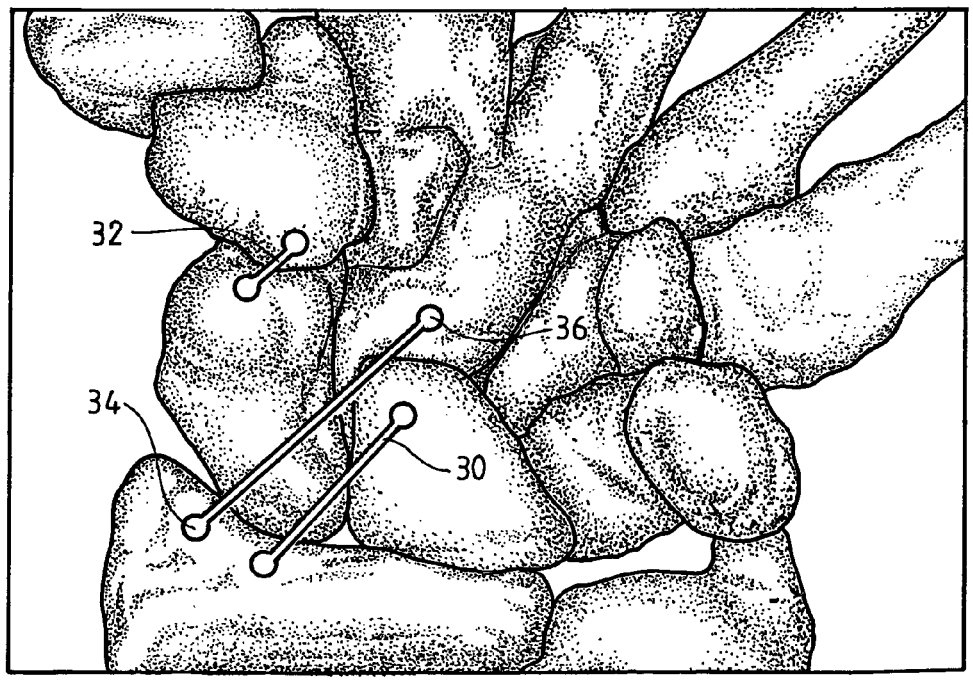
FIG. 11 depicts the same isometric points of those in FIG. 8 with the lateral carpal column of the wrist in extreme ulnar deviation.

Referring to FIGS. 10 and 11, three pairs of points have been identified, and a line 30 between the first pair of points extends between the radius 12 and the lunate 14, a line 32 extends between a second pair of points the first on the scaphoid 18 and the second on the trapezium 20, and the third line 34 extends between the radius 12 and the capitate 36.

As can be seen pictorially those same pairs of points are joined by paths that are the same length (isometric) with the change in position of the wrist from an extreme radial deviation to an extreme ulnar deviation (FIG. 10 to FIG. 11).

Clearly such analysis need not be confined to the carpus as the skeletal anatomy other body parts is just as amenable to this type of analysis.

To recognise and be able to quantify the relationship between bones and ligaments provides real benefits to the clinician.

Firstly, it will be possible to scan a contra lateral limb of the same patient or use a model of a standard wrist and compare them with the damaged wrist. Isometric points as determined by the computer for the contra lateral limb can be compared with one or more isometric points identified on the damaged or diseased limb of the same patient. Comparison can also be made to a collection of reference wrists. If certain pairs of points are not identified it is possible to conclude that certain ligaments are damaged in certain ways or that certain ligaments are not being kept in tension when they should be.

More particularly, based on extensive analysis of a broad-section of the population the program can quickly narrow down isometric points by using a model to predict typical isometric points for certain body parts in which case the computer can more readily identify where to begin it search for isometric points.

Thus, if for example, an isometric point can not be identified on a damaged wrist because the lunate translates in a particular direction, it cannot only be deducted that there is ligament damage or disease, but the degree of translation can indicate the degree of the actual damage or disease of a particular ligament.

By way of further example, a tearing or stretching of a ligament may cause another ligament to be loose and by use of a virtual model it is possible to identify which of those ligaments are torn and which of those is caused to be loose.

To be able to quantify ligament damage, not only allows the clinician to suggest an appropriate repair mechanism it is also possible for the degree of healing after treatment to be readily determined.

Yet furthermore it is possible for a surgeon to conduct a "what if" analysis on the 3-dimensional surface model of a particular patient's bone structure. Thus, if a particular ligament is damaged, it is possible to experiment in the virtual domain, with the effects of virtual surgery so as to test the results of that virtual surgery.

For example, if the surgeon thought a reconstruction of a ligament by partial tendon transfer was in order they could ensure that they have correctly identified the optimal fixing point of the tendon to a particular bone.

In a further example, the surgeon may experiment by virtually fusing two or more bones together at a particular point or points to regulate bone movement in a way different to that which is normal but which may restore acceptable function to the movement of other bones.

In such a circumstance, it is also possible by performing isometric point analysis again on the wrist that has had virtual surgery, to provide predictions as to the outcome of that intended surgery. Certain types of surgery can be performed in the digital environment and a realistic understanding of the result can be provided to not only the surgeon but also the patient about the expected functionality of the repaired body part following surgery.

Indeed, as a result of this approach, there may be choices and preferences for the surgeon and patient, which can be made, based solely on the predicted outcome of surgery, using the method of the invention.

It is also possible to create a model of the expected motion of one or more of the bones being examined. Such a model can be based on various rules developed from careful analysis of the 3-dimensional representations created by the method(s) described above.

For example, once the 3-dimensional representation of a particular bone is created certain points in or on its surface can be identified either by judicious choice or repeated experimentation, such that it is possible to determine certain rules of movement associated with those points. For example, a point on the lunate may only move linearly or within a small but defined deviation from a line. Such a rule defines by way of limitation a characteristic of the motion of that bone. There exist many other points in or on certain bones that will have certain quantifiable limits of movement and that therefore can be defined by a rule of motion.

This approach is commonly referred to as Rules Based Modelling and it is a matter of judicious selection which rules should be created and how they are applied.

The mass of the component bones as well as their characteristic shape, size and orientation can be included in the rules.

The extent to which bones can interact with adjacent bones in regards to proximity and collision avoidance and inter-bone compression tolerance given the particular (typically modest) deformity characteristics of the surface of the bones in question can be included.

Fixed distance constraints (isometric constraints) between points or regions on adjacent and non-adjacent bones can form the basis of one or more rules. These constraints most likely represent the action of various ligaments working with various bones. Knowledge of the variance of an expected isometric relationship is indicative of, for example, the physiological elasticity of one or more of the related ligamentous constraint elements.

Load points at which force can be applied to move various objects in a specific and thus predicable way can be used as part on the model. Indeed the expected deviation of certain points on bones can be quantified, even from patient to patient and a model of the typical patient created.

The complexity of any model has a direct correlation to the quantity of rules and the acceptable accuracy of the model will determine how complex the model needs to be. Thus certain models will, although not as accurate as others still provide results in circumstances that are still clinically acceptable.

Thus, in the context of this invention, it will be appreciated that once a suitable typical model or selection of models is available, it will be possible to further enhance the method(s) of clinical analysis disclosed previously.

The model of a typical wrist can be used in several ways.

One way is to create a model which is representative of a typical wrist and compare it with the 3-dimensional representations obtained of a patient's wrist.

Abnormalities may be readily identified if the typical wrist model is not the same as the performance of the patient's and the parameters of the model that are different (under or over value) can help to identify the abnormality and may also quantify the abnormality.

Another way is to create the 3-dimensional representations of a patient's wrist in accord with the method(s) described and apply the parameters of the model to the representation and create a free flowing representation of that patient's wrist. A single scanned image of the patient's wrist may suffice, but preferably at least two scanned images in extreme positions can be used as the basis for the application of the model. This approach can not only speed up diagnosis but also dramatically reduce costs while delivering clinically acceptable and useable results.

Thus, beyond analysis and "what if" manipulation of the multiply scanned wrist previously described, it is possible to manipulate a patient's modelled wrist in a virtual environment upon which virtual surgery can be performed as previously described.

Clearly, if the wrist of the patient is damaged or diseased such that it falls outside the parameters of an existing model the simple process of comparison will enable the development of a custom model for that patient. Once a unique virtual model of the wrist of that patient is created virtual surgery can be performed on that particular wrist and its working tested and virtual modifications conducted using pre and post surgery models.

Rules Based Modelling is but one convenient way of creating a further tool to assist the clinician and surgeon repairing or ameliorating the particular ailment of a patient.

Yet further, such a display and structural analysis of bone structure is most useful for teaching purposes thus opening a greater understanding of what heretofore has been a very specialist and not totally understood field.

It will be appreciated by those skilled in the art, that the invention is not restricted in its use to the particular application described and neither is the present invention restricted in this preferred embodiment with regard to the particular elements and/or features described and depicted herein. It will be appreciated that various modifications can be made without departing from the principle of the invention, therefore, the invention should be understood to include all such modifications within its scope.

The claims defining the invention are as follows:

1. A method of producing 3-dimensional visualisations of digital representations of cross-sectional slices of a vertebrate animal or human body part includes the steps of:
   a) obtaining a first ordered series of slices of a portion of said body part in a first position;
   b) applying one or more filters to each of said digital representations of said first ordered series of slices to identify the skeletal portions of said body part;
   c) converting said first filtered series into a 3-dimensional representation of the skeleton of said body part in said first position;
   d) obtaining a second ordered series of slices of said portion of said body part in a second position different to said first position wherein said first and said second position of said portion of said body part is representative of extremes of the achievable movement of said portion of said body part;
   e) applying one or more filters to each of said digital representations of said second ordered series of slices to identify the skeletal portions of said body part;
   f) converting said second filtered series into a 3-dimensional representation of the skeleton of said body part in said second position;
   g) combining said 3-dimensional representations to form a step frame animation having as many steps as there are ordered series of slices.

2. A method according to claim 1 further includes the further steps of:
   h) obtaining a one or more further ordered series of slices of said portion of said body part in a one or more further positions between the extremes of the achievable movement;
   i) converting said further filtered series into a 3-dimensional representation of the skeleton of said body part in said further positions;
   j) combining said 3-dimensional representations to form a step frame animation having as many steps as there are ordered series of slices.

3. A method according to claim 1 further includes the steps of:
   k) selecting a plurality of points on two or more skeletal object s in each said 3-dimensional representation; and
   l) analysing whether the distance between pairs of said points on different skeletal objects are isometric, if the distance between pairs of points remain the same or within a predetermined variance of distance during said step frame animation.

4. A method according to claim 3 further includes the step of:
   m) comparing the changes, if any, of the distances between predetermined pairs of points with expected changes, wherein the result of said comparison provides assistance to a cliniclan to form a diagnosis regarding the body part.

5. A method according to claim 3 wherein isometric points determined equate substantially to the fixation location of the ends of ligaments associated with said portion of said body part and the further step of:
   n) comparing the isometric points determined in step 3 to predetermined isometric points of a typical or contralateral body part and if said isometric points vary a greater than a predetermined amount a problem or abnormality or a degree of problem or abnormality associated with one or more ligaments associated with said portion of said body part exists.

6. A method according to claim 1 wherein step b and/or e includes a filter that allows an anatomically knowledgeable medical professional to adjust the bone selection criteria of said filter until a representation of adjacent bones shows that said adjacent bones are separate from one another.

7. A method according to claim 6 wherein said filter that allows an anatomically knowledgeable medical professional to adjust the density range criteria of said filter until a representation of adjacent bones shows that said adjacent bones are separate from one another.

8. A method according to claim 1 wherein said digital representation of slices of a vertebrate animal or human body part is provided by CAT/CT or MRI apparatus.

9. A method of producing 3-dimensional visualisations of digital representations of cross-sectional slices of a vertebrate animal or human body part includes the steps of:
   a) obtaining a first ordered series of slices of a portion of said body part in a first position;
   b) applying one or more filters to each of said digital representations of said first ordered series of slices to identify the skeletal portions of said body part;
   c) converting said first filtered series into a 3-dimensional representation of the skeleton of said body part in said first position;
   d) obtaining a second ordered series of slices of said portion of said body part in a second position wherein said first and said second position of said portion of said body part is representative of extremes of the achievable movement of said portion of said body part;
   e) applying one or more filters to each of said digital representations of said second ordered series of slices to identify the skeletal portions of said body part;
   f) converting said second filtered series into a 3-dimensional representation of the skeleton of said body part in said second position;
   g) applying to one or more points on the skeleton of said body part of each said 3-dimensional representation, one or more rules based animation constraints;
   h) creating a 3-dimensional animation of the movement of said body part according to said constraints.

10. A method according to claim 9 further includes the further steps of:
    i) obtaining a one or more further ordered series of slices of said portion of said body part in a one or more further positions between the extremes of the achievable movement;
    j) converting said further filtered series into a 3-dimensional representation of the skeleton of said body part in said further positions;
    k) combining said 3-dimensional representations to form a step frame animation having as many steps as there are ordered series of slices according to said rules based animation constraints.

11. A method according to claim 9, wherein step b and/or e of claim 10 includes a filter that allows an anatomically knowledgeable medical professional to adjust the bone selection criteria of said filter until a representation of adjacent bones shows that said adjacent bones are separate from one another.

12. A method according to claim 9, wherein said digital representation of slices of a vertebrate animal or human body part is provided by CAT/CT or MRI apparatus.

* * * * *